United States Patent
Saito et al.

(10) Patent No.: US 11,331,640 B2
(45) Date of Patent: *May 17, 2022

(54) MICROCAPSULE AND METHOD FOR PRODUCING THE SAME

(71) Applicant: Shin-Etsu Chemical Co., Ltd., Kamisu (JP)

(72) Inventors: Hiroaki Saito, Kamisu (JP); Toshihiko Kawakubo, Kamisu (JP)

(73) Assignee: Shin-Etsu Chemical Co., Ltd., Kamisu (JP)

( * ) Notice: Subject to any disclaimer, the term of this patent is extended or adjusted under 35 U.S.C. 154(b) by 99 days.

This patent is subject to a terminal disclaimer.

(21) Appl. No.: 16/781,004

(22) Filed: Feb. 4, 2020

(65) Prior Publication Data

US 2020/0276554 A1    Sep. 3, 2020

(30) Foreign Application Priority Data

Mar. 1, 2019 (JP) .............................. JP2019-037343

(51) Int. Cl.
- *C08L 1/28* (2006.01)
- *B01J 13/08* (2006.01)
- *C08L 27/06* (2006.01)

(52) U.S. Cl.
CPC ................. *B01J 13/08* (2013.01); *C08L 1/28* (2013.01); *C08L 27/06* (2013.01); *C08L 2205/025* (2013.01); *C08L 2205/03* (2013.01); *C08L 2205/20* (2013.01)

(58) Field of Classification Search
CPC .. A61K 8/11; A61K 9/5026; A61K 2800/652; A61K 2800/412; A61K 8/8123; A61K 8/38; C08L 2205/20; C08L 27/06; C08L 2205/03; C08L 2205/025; B01J 13/08; B01J 13/04
USPC ........................................................ 523/207
See application file for complete search history.

(56) References Cited

U.S. PATENT DOCUMENTS

| | | | |
|---|---|---|---|
| 4,898,781 A * | 2/1990 | Onouchi ................... | A61K 8/11 424/94.3 |
| 9,725,684 B2 * | 8/2017 | Fernandes .......... | C11D 17/0039 |
| 2012/0248639 A1 | 10/2012 | Akagawa et al. | |
| 2014/0200315 A1 | 7/2014 | Akagawa et al. | |
| 2019/0299186 A1 | 10/2019 | Mishiro et al. | |
| 2020/0277416 A1 * | 9/2020 | Saito ........................ | C08L 39/06 |

FOREIGN PATENT DOCUMENTS

| | | |
|---|---|---|
| EP | 3 556 780 A1 | 10/2019 |
| JP | 4-48926 A | 2/1992 |
| JP | 4-293904 A | 10/1992 |
| JP | 8-3206 A | 1/1996 |
| JP | 4688991 B2 | 5/2011 |
| WO | WO 84/01919 A1 | 5/1984 |

OTHER PUBLICATIONS

Extended European Search Report dated May 28, 2020 in corresponding European Patent Application No. 20160153.1, 7 pages.
Hyeon Jin Kwon et al., "Encapsulation of Peroxide Initiator in a Polyurea Shell: Its Characteristics and Effect on MMA Polymerization Kinetics", Macromolecular Research, Polymer Society of Korea. Seoul, KR, vol. 27, No. 2, Feb. 19, 2019, pp. 198-204.
Office Action dated Nov. 30, 2021 in Japanese Patent Application 2019-037343 with English Translation, 6 pages.

* cited by examiner

*Primary Examiner* — Hannah J Pak
(74) *Attorney, Agent, or Firm* — Oblon, McClelland, Maier & Neustadt, L.L.P.

(57) ABSTRACT

A microcapsule includes a core/shell structure, in which the shell includes a water-soluble polymer and the core includes an organic peroxide. The water-soluble polymer is preferably at least one water-soluble polymer selected from the group consisting of polyvinyl alcohol, gelatin, poly(meth) acrylic acid derivatives, polyvinyl pyrrolidone, and polyethylene oxide. The polyvinyl alcohol is preferably partially saponified polyvinyl alcohol having a degree of saponification of 80% by mole or more and 99.5% by mole or less and an average degree of polymerization of 1,500 or more and 3,500 or less.

7 Claims, No Drawings

US 11,331,640 B2

MICROCAPSULE AND METHOD FOR PRODUCING THE SAME

CROSS-REFERENCE TO RELATED APPLICATION(S)

The present application claims priority to and incorporates by reference the entire contents of Japanese Patent Application No. 2019-037343 filed in Japan on Mar. 1, 2019.

BACKGROUND OF THE INVENTION

1. Field of the Invention

The present invention relates to a microcapsule and a method for producing the same.

2. Description of the Related Art

Conventionally, an organic peroxide has been known as a polymerization initiator of a vinyl monomer (for example, a vinyl chloride monomer) by radical reaction. The organic peroxide diluted with an organic solvent or emulsified with water has an easy handling and excellent safety and thus is put into practical use.

In general, the polymerization of the vinyl chloride monomer or the polymerization of the vinyl chloride monomer and a monomer that can be copolymerized with the vinyl chloride monomer is carried out by a batch-wise suspension polymerization method. More specifically, the batch-wise suspension polymerization method is a method for charging an aqueous medium, the monomer, and a dispersion agent (suspension agent) into a polymerization reactor, subsequently charging the polymerization initiator in the form described above, and subsequently raising a temperature inside the polymerization reactor to a predetermined polymerization reaction temperature by flowing hot water through a jacket to carry out the polymerization reaction.

In recent years, in the production of a vinyl chloride polymer, a larger polymerization reactor has been formed and a reaction time has been shortened for the purpose of an increase in productivity. As one of the methods for shortening the reaction time, a method for raising a polymerization rate by increasing the amount of the polymerization initiator to be charged is exemplified. However, as the amount of the polymerization initiator is increased in the polymerization reactor having a larger size, it takes time for the polymerization initiator to be uniformly dispersed in the polymerization reactor. Consequently, the nonuniform concentration distribution of the polymerization initiator is generated. This causes the problem of partially generating particles having less internal pore called glassy particles and increasing the number of fish eyes.

As another method for shortening the polymerization time, a method for previously charging the vinyl chloride monomer, and subsequently continuously charging warm water to shorten the temperature rising time and increase the productivity is exemplified. This method allows the internal temperature at the time of the completion of warm water charge to be adjusted to some extent by the temperature of the warm water to be charged. As described above, the temperature rising time can be substantially shortened by adjusting the internal temperature at the time of the completion of the charge to approximately the predetermined polymerization temperature (in the present specification, this method is also called a high temperature water-charged polymerization method). However, this method has higher temperature inside the polymerization reactor at the time of charging the polymerization initiator than that of the conventional method and thus the polymerization reaction is rapidly promoted in the vicinity of the place where the polymerization initiator is charged. As a result, the problem of more easily generating the non-uniformity of the concentration distribution of the polymerization initiator and thus increasing the number of fish eyes has arisen.

The vinyl chloride polymer is a useful resin that is inexpensive and has excellent physical properties and is used for a wide range of applications such as a soft product field and a hard product field. Examples of the applications include a coated electric wire, a lap film, and a sheet in the soft product field. The surface of the products such as the lap film and the sheet should be smooth and, in particular, the generation of the fish eyes should be avoided. With respect to the particles forming the fish eyes, foreign matters except the resin such as contamination and a resin generated by partially heating in high intensity at the drying process in the production process of the vinyl chloride polymer are some of the causes. On the other hand, not dissolving such fish eyes but making the vinyl chloride polymer particles themselves generated in the polymerization reactor be difficult to form fish eyes has also been tried.

Specifically, it has been well known that the production of the vinyl chloride polymer having an excellent plasticizer absorption property results in reduction in fish eyes. Many methods for producing the vinyl chloride polymer having an excellent plasticizer absorption property have been reported. For example, Japanese Patent Application Laid-open No. H8-3206 has described simultaneous use of (1) partially saponified polyvinyl alcohol having an average degree of polymerization of 150 to 600 and a degree of saponification of 20% by mole to 55% by mole and (2) hydroxypropyl methylcellulose having a methoxy group content of 19% by weight to 30% by weight, a hydroxypropoxy group content of 4% by weight to 15% by weight, and a viscosity of a 2% by weight aqueous solution of the hydroxypropyl methylcellulose at 20° C. of 100 cps or more in a specific weight ratio. Specifically, Japanese Patent Application Laid-open No. H8-3206 has described that (1) and (2) are simultaneously used in a weight ratio of (1)/(2) of 2/1 to 5/1. As described above, a method for producing the porous vinyl chloride polymer having the excellent plasticizer absorption property by the suspension polymerization method has been developed. However, use of a large amount of polyvinyl alcohol having the small degree of saponification in the initial stage of the polymerization causes a risk in which capability of protecting the surface of the oil droplet of the vinyl chloride monomer immediately after the start of the polymerization may be rapidly deteriorated and thus the obtained polymer can form coarse particles. An increase in the amount of the dispersion agent to be used in order to prevent the coarse particle formation avoids generating the problem of forming the coarse particles. However, the surface of the oil droplet of the vinyl chloride monomer is covered with the thick film of the dispersion agent. As a result, the polymerization initiator taken in the oil droplet of the vinyl chloride monomer is difficult to aggregate with another oil droplet of the vinyl chloride monomer and difficult to disperse and thus non-uniformity of the concentration distribution of the polymerization initiator is generated to increase the fish eyes.

Japanese Patent No. 4688991 has described the use of 0.04 part by mass to 0.08 part by mass of partially saponified polyvinyl alcohol (A) having an average degree of polymerization of 2,000 to 3,000 and a degree of saponification of 75% by mole to 85% by mole relative to 100 parts by mass of the vinyl chloride monomer and 0.01 part by mass to 0.1 part by mass of partially saponified polyvinyl alcohol (B) having an average degree of polymerization of 100 to 700 and a degree of saponification of 20% by mole to 55% by mole relative to 100 parts by mass of the vinyl chloride monomer. Japanese Patent No. 4688991 has also described that 10% to 80% out of the total amount to be used of the partially saponified polyvinyl alcohol (A) is charged before the start of the polymerization and the remaining partially saponified polyvinyl alcohol (A) is added to the polymerization system at the time of reaching the polymerization conversion ratio to 1% to 10%. This allows the porous vinyl chloride polymer having the excellent plasticizer absorption property to be obtained. However, a risk of destabilizing the polymerization system depending on the amount of the suspension agent to be added during the polymerization or the timing of the addition and thus forming coarse particles of the obtained polymer may arise.

It can be said that the features of these conventional techniques are based on the devisal of the dispersion agent to be used in the production of the vinyl chloride polymer polymerized by the suspension polymerization. This is because the inside of the obtained vinyl chloride resin is possibly highly porous by devising the degree of the surface activation capacity of the dispersion agent to be used. It is not difficult to imagine that the high porous resin has a structure of easily absorbing a plasticizer into deeper inside. The resin having such a structure of easily absorbing a plasticizer into deeper inside may be easy to be entirely plasticized. Consequently, the resin is easy to be melted at the time of kneading and thus generation of the fish eyes is reduced.

However, such conventional techniques are not necessarily advantageous from the viewpoint of carrying out polymerization stably. This is because the action of avoiding agglomeration of the monomer oil droplets with each other in the suspension polymerization of the vinyl chloride polymer is possibly insufficient by using a dispersion agent having extremely high surface activation capacity or decreasing the amount of the dispersion agent added at the initial stage of the polymerization. The devisal of the dispersion agent to be used in the polymerization may result in providing a special product in which the basic properties of the obtained vinyl chloride polymer such as an average particle diameter, an amount of a plasticizer to be absorbed, and an apparent density are changed. Therefore, the conventional techniques are by no means desired from the viewpoint of production control.

As described above, the production methods described in Japanese Patent Application Laid-open No. H8-3206 and Japanese Patent No. 4688991 have problems of destabilization of the polymerization and change in the basic properties of the produced vinyl chloride polymer. Vinyl polymers other than the vinyl chloride polymer also have the same problems.

SUMMARY OF THE INVENTION

In view of the aforementioned, an object of the present invention is to provide a microcapsule that does not involve the problems of the destabilization of the polymerization and the change in the basic properties of the produced vinyl chloride polymer and can reduce fish eyes in the produced vinyl polymer.

A microcapsule according to one aspect of the present invention includes a core/shell structure, wherein the shell includes a water-soluble polymer and the core includes an organic peroxide.

According to another aspect of the present invention, in the microcapsule, it is preferable that the water-soluble polymer is at least one water-soluble polymer selected from the group consisting of polyvinyl alcohol, gelatin, poly (meth)acrylic acid derivatives, polyvinyl pyrrolidone, and polyethylene oxide.

According to still another aspect of the present invention, in the microcapsule, it is preferable that the polyvinyl alcohol is partially saponified polyvinyl alcohol having a degree of saponification of 80% by mole or more and 99.5% by mole or less and an average degree of polymerization of 1,500 or more and 3,500 or less.

According to still another aspect of the present invention, in the microcapsule, it is preferable that the microcapsule has a median diameter (D50) of 15 μm or less.

According to still another aspect of the present invention, in the microcapsule, it is preferable that the organic peroxide has a 10-hour half-life temperature in benzene at a concentration of 0.1 mol/L of 70° C. or less.

A method for producing a microcapsule according to still another aspect of the present invention includes a mixing step of mixing a water-soluble polymer and an organic peroxide to give a microcapsule, wherein the microcapsule has a core/shell structure, and the shell includes the water-soluble polymer and the core includes the organic peroxide.

According to still another aspect of the present invention, in the method for producing a microcapsule, it is preferable that the in the mixing step, an aqueous medium is further mixed with the water-soluble polymer and the organic peroxide to give the microcapsule.

According to still another aspect of the present invention, in the method for producing a microcapsule, it is preferable that in the mixing step, the aqueous medium is used in an amount of 30 parts by mass or more and 150 parts by mass or less relative to the 100 parts by mass of the organic peroxide.

According to still another aspect of the present invention, in the method for producing a microcapsule, it is preferable that in the mixing step, the water-soluble polymer is used in an amount of 0.01 parts by mass or more and 25 parts by mass or less relative to the 100 parts by mass of the organic peroxide.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, the embodiment will be described in detail. It should be noted that the present invention is not limited at all by the following embodiment.

Microcapsule

The microcapsule according to the embodiment includes the core/shell structure, in which the shell includes a water-soluble polymer and the core includes the organic peroxide. As described above, in the microcapsule according to the embodiment, the organic peroxide is encapsulated. In other words, the microcapsule is a coated particle-like substance having a particle-like substance including the organic peroxide and the coated layer including the water-soluble polymer attached to the surface of the particle-like substance. The formation of the core/shell structure can be confirmed by the solubility of the microcapsule to ethylene dichloride (EDC) described in Examples below. The microcapsule according to the embodiment is dispersed in, for example, an aqueous medium and forms a composition together with the aqueous medium.

At the time of the production of the vinyl polymer, use of the microcapsule according to the embodiment allows the concentration distribution of the organic peroxide having a role as the polymerization initiator to be uniform in the polymerization reactor. This allows the fish eyes in the produced vinyl polymer to be reduced.

As described above, use of the microcapsule according to the embodiment allows the reduction in the fish eyes in the vinyl polymer to be achieved without devising the dispersion agent. In other words, use of the microcapsule according to the embodiment allows the reduction in the fish eyes in the vinyl polymer to be achieved without concerns about the coarse particle formation associated with the reduction in polymerization stability and, in addition, without concerns about the change in the basic properties in the vinyl polymer.

As described above, with regard to the particles forming the fish eyes, foreign matters except the resin such as contamination and a resin generated by partially heating in high intensity at the drying process in the production process of the vinyl chloride polymer are some of the causes. However, the present embodiment does not aim to dissolve such fish eyes but aims to make the vinyl chloride polymer particles themselves generated due to non-uniformity of the concentration distribution of the polymerization initiator in the polymerization reactor difficult to form the fish eyes. Use of the microcapsule according to the embodiment allows this object to be achieved. The embodiment also has a feature of easily removing the remaining monomer in the vinyl polymer and providing a scale prevention effect.

Hereinafter, the microcapsule according to the embodiment will be described more specifically. The water-soluble polymer included in the shell is preferably at least one water-soluble polymer selected from the group consisting of polyvinyl alcohol, gelatin, poly(meth)acrylic acid derivatives, polyvinyl pyrrolidone, and polyethylene oxide. The water-soluble polymers may be used singly or may be used in combination of two or more of them.

Polyvinyl alcohol is usually produced by saponifying a vinyl ester polymer using a known method.

A vinyl ester monomer is not particularly limited and examples of the vinyl ester monomer may include fatty acid vinyl esters such as vinyl acetate, vinyl formate, vinyl propionate, vinyl caprylate, and vinyl versatate. These monomers may be used singly or in combination of two or more of them.

At the time of polymerizing the vinyl ester monomer, the vinyl ester monomer may be copolymerized with other monomers. The other monomers that can be used are not particularly limited. Examples of the other monomers include α-olefins, acrylic acid and the salts thereof, acrylic acid esters, methacrylic acid and the salts thereof, methacrylic acid esters, acrylamide, acrylamide derivatives, methacrylamide, methacrylamide derivatives, vinyl ethers, nitriles, vinyl halides, vinylidene halides, allyl compounds, unsaturated dicarboxylic acid and the salts thereof or the esters thereof, olefin sulfonic acids and the salts thereof, vinyl silyl compounds, and fatty acid alkyl esters. These other monomers may be used singly or in combination of two or more of them.

At the time of the polymerization of the vinyl ester polymer, a chain transfer agent may coexist for the purpose of, for example, adjusting the degree of polymerization of the vinyl ester polymer to be obtained. The chain transfer agent is not particularly limited. Examples of the chain transfer agent include aldehydes such as acetaldehyde, propionaldehyde, butyraldehyde, and benzaldehyde; ketones such as acetone, methyl ethyl ketone, hexanone, and cyclohexanone; mercaptans such as 2-hydroxyethanethiol and dodecyl mercaptan; and organic halides such as carbon tetrachloride, carbon tetrabromide, dichloromethane, dibromomethane, trichloroethylene, and perchlorethylene. These chain transfer agents may be used singly or in combination of two or more of them.

The polyvinyl alcohol may be polyvinyl alcohol provided by modifying after production of polyvinyl alcohol by the methods of acetoacetic esterification, acetalization, urethaneization, etherification, grafting, phosphate esterification, and oxyalkyleneation of polyvinyl alcohol, that is, modified polyvinyl alcohol.

Examples of the poly(meth)acrylic acid derivatives include polyacrylic acid salts, polyacrylamide, and polyacrylic acid esters. Examples of the polyacrylic acid salts include salts formed of a polyacrylic acid and a monovalent cation. Examples of the monovalent cation include $Li^+$, $Na^+$, $K^+$, and $NH_4^+$. Examples of the polyacrylic acid esters include polyacrylic acid alkyl esters. The alkyl group in the polyacrylic acid alkyl esters is preferably an alkyl group having a carbon atom number of 1 to 5 and more preferably an alkyl group having a carbon atom number of 1 to 3.

Of these polymers, partially saponified polyvinyl alcohol is suitably used as the water-soluble polymer because the fish eyes in the produced vinyl polymer can be more reduced.

The partially saponified polyvinyl alcohol preferably has a degree of saponification of 80% by mole or more and 99.5% by mole or less. The degree of saponification can be determined in accordance with the degree of saponification measurement method of polyvinyl alcohol prescribed in JIS K 6726. A degree of saponification of less than 80% by mole may cause dissolution of the shell with the aqueous medium before the polymerization initiator is uniformly dispersed in the polymerization reactor. This may cause nonuniform concentration distribution of the polymerization initiator and thus the fish eyes may be increased in the produced vinyl polymer. On the other hand, a degree of saponification of more than 99.5% by mole may be unfavorable from an economic standpoint due to requiring much energy for heating and dissolution.

The partially saponified polyvinyl alcohol preferably has an average degree of polymerization of 1,500 or more and 3,500 or less. The average degree of polymerization can be determined in accordance with the average degree of polymerization measurement method of polyvinyl alcohol prescribed in JIS K 6726. A degree of polymerization of less than 1,500 may cause dissolution of the shell with the aqueous medium before the polymerization initiator is uniformly dispersed in the polymerization reactor. This may cause nonuniform concentration distribution of the polymerization initiator and thus the fish eyes may be increased in the produced vinyl polymer. In particular, in the case of high temperature water charge polymerization method, this tendency becomes remarkable and significant increase in fish eyes may occur. On the other hand, a degree of polymerization of more than 3,500 may result in requiring excessive time for dissolving the shell and thus also requiring excessive time for penetrating the polymerization initiator into the oil droplet of the vinyl monomer. Therefore, although the fish eyes can be reduced, polymerization time becomes longer and thus productivity may deteriorate, which is unfavorable.

The organic peroxide included in the core preferably has a 10-hour half-life temperature in benzene at a concentration of 0.1 mol/L of 70° C. or less and more preferably 30° C. or more and 70° C. or less. A 10-hour half-life temperature of more than 70° C. requires an excessively large amount of the organic peroxide and thus may result in deteriorating the initial colorability, extraction resistance, and the like of the produced vinyl polymer. On the other hand, a 10-hour half-life temperature of less than 30° C. may cause the activity of the organic peroxide serving as the polymerization initiator to be difficult to retain. In the present specification, the 10-hour half-life temperature is also called T10-HDT.

Specific examples of the organic peroxide include a diacyl peroxide compound, a peroxydicarbonate compound, and a peroxyester compound, which have the 10-hour half-life temperature within the above range. The organic peroxides may be used singly or may be used in combination of two or more of them.

Examples of the diacyl peroxide compound include a compound represented by the following general formula (1).

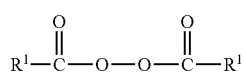
(1)

In the formula (1), two Fes may be the same as or different from each other and are substituted or unsubstituted alkyl groups having a carbon atom number of 1 to 12. The alkyl groups may be linear, branched, or cyclic. Examples of the alkyl groups include n-alkyl groups such as a methyl group, an ethyl group, a n-propyl group, a n-butyl group, a n-pentyl group, a n-hexyl group, a n-heptyl group, a n-octyl group, a n-nonyl group, a n-decyl group, a n-undecyl group, and a n-dodecyl group; sec-alkyl groups; tert-alky groups such as a tert-butyl group, a tert-pentyl group, a tert-hexyl group, a tert-nonyl group, and a tert-decyl group; isoalkyl groups such as an isopropyl group, an isobutyl group, an isopentyl group, an isoheptyl group, and an isooctyl group; cycloalkyl groups such as a 1-cyclohexyl-1-methylethyl group; and a 2,4,4-trimethylpentyl group.

As the diacyl peroxide compound, more specifically dilauroyl peroxide (T10-HDT=62° C.), di(3,5,5-trimethylhexanoyl)peroxide (T10-HDT=59° C.), diisobutyl peroxide (T10-HDT=33° C.), and disuccinic acid peroxide (T10-HDT=65° C.), and the like are suitably used.

Examples of the peroxydicarbonate compound include a compound represented by the following general formula (2).

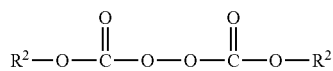
(2)

In the formula (2), two $R^2$s may be the same as or different from each other and are substituted or unsubstituted alkyl groups having a carbon atom number of 1 to 10. The alkyl groups may be linear, branched, or cyclic. Examples of the alkyl groups include n-alkyl groups such as a methyl group, an ethyl group, a n-propyl group, a n-butyl group, a n-pentyl group, a n-hexyl group, a n-heptyl group, a n-octyl group, a n-nonyl group, and a n-decyl group; sec-alkyl groups; tert-alky groups such as a tert-butyl group, a tert-pentyl group, a tert-hexyl group, a tert-nonyl group, and a tert-decyl group; isoalkyl groups such as an isopropyl group, an isobutyl group, an isopentyl group, an isoheptyl group, and an isooctyl group; cycloalkyl groups such as a 1-cyclohexyl-1-methylethyl group; and a 2,4,4-trimethylpentyl group.

As the peroxydicarbonate compound, more specifically di-(2-ethylhexyl)peroxydicarbonate (T10-HDT=44° C.), di-n-propyl peroxydicarbonate (T10-HDT=40° C.), diisopropyl peroxydicarbonate (T10-HDT=41° C.), di-(4-t-butylcyclohexyl)peroxydicarbonate (T10-HDT=41° C.), di-sec-butyl peroxydicarbonate (T10-HDT=41° C.), and the like are suitably used.

Examples of the peroxyester compound include a compound represented by the following general formula (3).

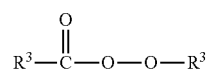
(3)

In the formula (3), two $R^3$s may be the same as or different from each other and are substituted or unsubstituted alkyl groups having a carbon atom number of 1 to 10 or aralkyl groups having a carbon atom number of 7 to 10. The alkyl groups may be linear, branched, or cyclic. Examples of the alkyl groups include n-alkyl groups such as a methyl group, an ethyl group, a n-propyl group, a n-butyl group, a n-pentyl group, a n-hexyl group, a n-heptyl group, a n-octyl group, a n-nonyl group, and a n-decyl group; sec-alkyl groups; tert-alky groups such as a tert-butyl group, a tert-pentyl group, a tert-hexyl group, a tert-nonyl group, and a tert-decyl group; isoalkyl groups such as an isopropyl group, an isobutyl group, an isopentyl group, an isoheptyl group, and an isooctyl group; cycloalkyl groups such as a 1-cyclohexyl-1-methylethyl group; a 2,4,4-trimethylpentyl group; and examples of the aralkyl groups include groups such as a 2-phenylpropan-2-yl group.

As the peroxyester compound, more specifically t-butyl peroxyneodecanoate (T10-HDT=46° C.), t-hexyl peroxyneodecanoate (T10-HDT=45° C.), t-butyl peroxypivalate (T10-HDT=54.6° C.), t-hexyl peroxypivalate (T10-HDT=53° C.), α-cumyl peroxyneodecanoate (T10-HDT=37° C.), t-butyl peroxyneoheptanoate (T10-HDT=51° C.), t-amyl peroxyneodecanoate (T10-HDT=43° C.), 1,1,3,3-tetramethylbutyl peroxyneodecanoate (T10-HDT=41° C.), 1,1,3,3-tetramethylbutyl peroxypivalate (T10-HDT=48° C.), and the like are suitably used.

The 10-hour half-life temperature (T10-HDT) can be determined as follows. A benzene solution in which the organic peroxide concentration is 0.1 mol/L is prepared. The solution is sealed in a glass tube purged with nitrogen and the tube was immersed into a constant temperature bath adjusted to the predetermined temperature to thermally decompose the organic peroxide. The change in the concentration of the organic peroxide relative to time is measured. In the reaction conditions, the decomposition reaction of the organic peroxide can be approximately treated as a first-order reaction and thus the following formulas (4) and (5) are true.

$$dx/dt = k(a-x) \tag{4}$$

$$\ln[a/(a-x)] = kt \tag{5}$$

In the two formulas (4) and (5), x represents the concentration of the decomposed organic peroxide, a represents the initial concentration of the organic peroxide, k represents a decomposition rate constant, and t represents time. The half-life refers to a time required to decrease the organic peroxide concentration to a half of the initial concentration by decomposition. Therefore, the half-life is represented by $t_{1/2}$ and a/2 is substituted for x in the formula (5) to obtain the following relational formula.

$$kt_{1/2} = \ln 2 \quad (6)$$

From the concentration change of the organic peroxide measured above, the relation between the time t and ln [a/(a−x)] is plotted. The gradient of the obtained straight line is determined to be k and thus the half-life $t_{1/2}$ is determined at the temperature from the formula (6). Therefore, the 10-hour half-life temperature can be determined as a temperature at which $t_{1/2}$ of a certain organic peroxide is 10 hours.

The particle diameter of the microcapsule is not particularly limited. The median diameter (D50) of the microcapsule is preferably 15 μm or less and more preferably 0.5 μm or more and 15 μm or less. The median diameter (D50) within the above range allows the storage stability of the microcapsule in which the organic peroxide in the aqueous medium is encapsulated to be more secured.

As described above, the microcapsule according to the embodiment is, for example, dispersed in the aqueous medium to form the composition together with the aqueous medium. The content of the organic peroxide in the composition (aqueous liquid) is usually 10% by mass or more and 70% by mass or less and preferably 15% by mass or more and 65% by mass or less, and more preferably 30% by mass or more and 60% by mass or less. A content of the organic peroxide of less than 10% by mass may result in high transport cost and thus may be unfavorable from an economic standpoint.

Examples of the aqueous medium include water such as clean water, ion-exchanged water, distilled water, and ultrapure water and mixed media of water with a water-soluble organic solvent. Examples of the water-soluble organic solvent include alcohols such as methanol, ethanol, n-propanol, isopropanol (2-propanol), ethylene glycol, and diethylene glycol. In the case where the aqueous medium is the mixed medium, the content of the water-soluble organic solvent in the aqueous medium is preferably more than 0% by mass and 50% by mass or less.

The microcapsule according to the embodiment is preferably prepared by an emulsion method. Specifically, the microcapsule can be prepared by rotationally mixing the water-soluble polymer (for example, the partially saponified polyvinyl alcohol), the organic peroxide, and the aqueous medium. Here, the rotation mixing is preferably carried out at high speed rotation and may be carried out while the number of rotation is appropriately being adjusted. The number of rotation is preferably 1,000 rpm or more and 3,000 rpm or less. The mixing can be suitably emulsified in −30° C. or more and 50° C. or less and preferably −20° C. or more and 30° C. or less for 30 seconds or more and 120 minutes or less. Consequently, the composition (the aqueous liquid) in which the microcapsule is dispersed in the aqueous medium is obtained.

An apparatus to be used may be a well-known apparatus. Examples of the usable apparatus include a mechanical rotation-type stirrer, a high speed rotation shear-type stirrer, a colloid mill, a pearl mill, a homogenizer, a pressurized homogenizer, an ultrasonic homogenizer, a homomixer, and a microfluidizer.

In the mixing, the aqueous medium is desirably used in an amount of 20 parts by mass or more and 180 parts by mass or less and more preferably in an amount of 30 parts by mass or more and 150 parts by mass or less relative to the 100 parts by mass of the organic peroxide.

In the mixing, the water-soluble polymer (for example, the partially saponified polyvinyl alcohol) is preferably used in an amount of 0.001 part by mass or more and 30 parts by mass or less and more preferably used in an amount of 0.01 part by mass or more and 25 parts by mass or less relative to 100 parts by mass of the organic peroxide.

In the mixing, the organic peroxide may be used by previously emulsifying with an isoparaffin solvent in order to dilute or dissolve the organic peroxide. In the mixing, a surfactant may be further added, if necessary.

The microcapsule according to the embodiment may be prepared by known microcapsule formation methods other than the emulsion method. Examples of the known microcapsule formation methods other than the emulsion method include a coacervation method, a spray drying method, a drying method in liquid, and an in-situ method.

Method for Producing Vinyl Polymer

The microcapsule according to the embodiment is suitably used for the production of the vinyl polymer. In other words, the method for producing the vinyl polymer includes a polymerization step of using the composition including the microcapsule and polymerizing the vinyl monomer by the radical reaction to give the vinyl polymer. As described above, the microcapsule has the core/shell structure, in which the shell includes the water-soluble polymer and the core includes the organic peroxide. By using the microcapsule according to the embodiment, the fish eyes can be reduced in the produced vinyl polymer.

Examples of the vinyl monomer include monomers such as vinyl chloride, styrene, (meth)acrylic esters, (meth)acrylic acid, and vinyl acetate. Vinyl chloride is suitably used. As the vinyl monomer, a vinyl monomer that can be copolymerized with vinyl chloride may be used together with vinyl chloride. Examples of the vinyl monomer that can be copolymerized with vinyl chloride include vinyl halides or vinylidene halides such as vinyl bromide and vinylidene chloride; α-olefins such as ethylene, propylene, 1-butene, 1-pentene, 1-hexene, 1-heptene, 1-octene, 1-nonene, 1-decene, 1-undecene, 1-dodecene, 1-tridecene, and 1-tetradecene, acrylic acid; acrylic acid esters such as methyl acrylate, ethyl acrylate, and butyl acrylate; vinyl esters such as vinyl acetate and vinyl propionate; vinyl ethers such as lauryl vinyl ether and isobutyl vinyl ether; and aromatic vinyls such as styrene. The vinyl monomers that can be copolymerized with vinyl chloride may be used singly or may be used in combination of two or more of them.

As described above, the vinyl polymer to be produced is preferably a vinyl chloride homopolymer using vinyl chloride alone as the vinyl monomer or a copolymer using vinyl chloride and the vinyl monomer that can be copolymerized with vinyl chloride as the vinyl monomers. In the case of the copolymer, usually vinyl chloride is used in an amount of 50% by mass or more in the vinyl monomers. In other words, in the method for producing the vinyl polymer, the polymerization step is preferably a step of polymerizing vinyl chloride as the vinyl monomer to give the vinyl chloride polymer (more specifically, the vinyl chloride homopolymer) as the vinyl polymer. Alternatively, the polymerization step is also preferably a step of polymerizing vinyl chloride and the vinyl monomer that can be copolymerized with vinyl chloride to provide the vinyl chloride polymer as the vinyl polymer.

The polymerization step is carried out by, for example, the suspension polymerization. The polymerization conditions are not particularly limited. For example, the vinyl monomer, the composition including the microcapsule, the suspension agent, and the aqueous medium are charged in the polymerization container and thereafter a temperature of the content in the polymerization container is raised to carry out the polymerization reaction while the content is being stirred. Specifically, the polymerization reaction is carried out at 20° C. to 80° C. for 1 hour to 20 hours.

The microcapsule encapsulating the organic peroxide is preferably used in an amount of 0.01 part by mass or more and 0.5 part by mass or less relative to 100 parts by mass of the vinyl monomer.

As the suspension agent charged into the polymerization container, specifically, the water-soluble polymer is used. Examples of the water-soluble polymer include water-soluble cellulose ethers such as methylcellulose, hydroxyethylcellulose, hydroxypropylcellulose, and hydroxypropylmethylcellulose; water-soluble or oil-soluble partially saponified polyvinyl alcohols; (meth)acrylic acid polymers; and gelatin. The suspension agents may be used singly or may be used in combination of two or more of them. The suspension agent is usually used in an amount of 0.02 part by mass or more and 5.0 parts by mass or less and preferably in an amount of 0.04 part by mass or more and 1.5 parts by mass or less relative to 100 parts by mass of the vinyl monomer.

Examples of the aqueous medium charged into the polymerization container include water such as clean water, ion-exchanged water, distilled water, and ultrapure water and mixed media of water with a water-soluble organic solvent. Examples of the water-soluble organic solvent include alcohols such as methanol, ethanol, n-propanol, isopropanol (2-propanol), ethylene glycol, and diethylene glycol. In the case where the aqueous medium is the mixed medium, the content of the water-soluble organic solvent in the aqueous medium is preferably more than 0% by mass and 50% by mass or less. The aqueous medium is usually used in an amount of 90 parts by mass or more and 250 parts by mass or less and preferably in an amount of 100 parts by mass or more and 200 parts by mass or less relative to 100 parts by mass of the vinyl monomer.

At the time of the polymerization, other additives may be added into the polymerization container, if necessary. Examples of the additives include oil-soluble polymerization initiators except the organic peroxides; adjusting agents for the degree of polymerization such as acetaldehyde, butyraldehyde, trichlorethylene, perchlorethylene, and mercaptans; and polymerization inhibitors such as phenol compounds, sulfur compounds, and N-oxide compounds. In addition, for example, pH adjusters, scale prevention agents, or crosslinking agent may be used as the additives. The additives may be used singly or may be used in combination of two or more of them.

The composition including the microcapsule may be collectively added or may be intermittently or continuously added to the polymerization container depending on the purpose of use. Each of the vinyl monomer, the suspension agent, and the aqueous medium may be charged on the way during the polymerization.

In the method for producing the vinyl polymer described above, the polymerization step may be carried out by using vinyl chloride in an amount of less than 50% by mass as the vinyl monomer. The polymerization step may be carried out not using vinyl chloride but using the vinyl monomer alone that can be copolymerized with vinyl chloride.

In the method for producing the vinyl polymer, the polymerization step may be carried out by a polymerization type except the suspension polymerization. Specifically, the polymerization type is not particularly limited as long as the radical polymerization reaction of the vinyl monomer can be carried out. Examples of the polymerization type may include emulsion polymerization, bulk polymerization, and fine suspension polymerization.

The present invention is not limited by the embodiment. Products constituted by appropriately combining the constituents described above are included in the present invention. Further effects and modification examples can be easily evolved by those skilled in the art. Thus, the wider aspect of the present invention is not limited by the embodiment and various modifications are possible.

EXAMPLES

Hereinafter, the embodiment will be described in detail based on Examples carried out in order to clarify the effect of the embodiment. The embodiment is not limited at all by Examples and Comparative Examples described below.

Example 1

(1) Production of Aqueous Liquid Including microcapsule

Into a 500 ml four-necked flask equipped with a common stirring device and a thermometer, 15 parts by mass of water, 10 parts by mass of the aqueous solution of partially saponified polyvinyl alcohol (concentration 10% by mass) having a degree of saponification of 88% by mole and an average degree of polymerization of 1,800, 17 parts by mass of ethanol, and 3 parts by mass of a surfactant (sorbitan monooleate) were charged and dissolved, and thereafter the temperature inside the flask was adjusted to 5° C. to 10° C. To this solution, 55 parts by mass of di-(2-ethylhexyl) peroxydicarbonate was added dropwise as the organic peroxide and the resultant mixture was vigorously stirred. The mixture was further stirred for 30 minutes to give an aqueous liquid (a microcapsule composition liquid) including the microcapsule into which di-(2-ethylhexyl)peroxydicarbonate was encapsulated. In Table 1, the median diameter (D50) of the obtained microcapsule measured with a laser diffraction type particle size distribution measuring apparatus is listed.

(2) Evaluation of Solubility to Ethylene Dichloride (EDC)

The solubility of the microcapsule to ethylene dichloride (EDC) was evaluated by the following method. Into a 500 ml beaker, 150 parts by mass of water, 50 parts by mass of the aqueous liquid including the microcapsule, and 100 parts by mass of EDC were charged and the resultant mixture was stirred using a common stirring device at an internal temperature of 40° C. for 5 minutes. Thereafter, the stirred mixture was allowed to stand. A state when the EDC phase and the water phase were separated was observed and the evaluated in accordance with the following criteria. The result is listed in Table 1.

○: A state where almost no microcapsule is dissolved in the EDC phase

Δ: A state where less than half of the total amount of the microcapsule is dissolved in the EDC phase x: A state where a half or more of the total amount of the microcapsule is dissolved in the EDC phase In order to reduce fish eyes in the produced vinyl polymer, formation of the microcapsule having the core/shell structure is required. In other words, it is required that the microcapsule is not immediately dissolved in the vinyl polymer but is dispersed in the aqueous medium for a certain period after the microcapsule is charged into the polymerization reactor. Therefore, using the suspension polymerization method of vinyl chloride as a model and EDC as a pseudo substance of vinyl chloride, the solubility of the microcapsule to EDC was evaluated. An excellent evaluation result allows formation of the microcapsule having the core/shell structure to be confirmed.

(3) Production of Vinyl Chloride Polymer

Into a stainless-steel polymerization reactor having an interior content of 2 m$^3$, 876 kg of deionized water, 182.5 g of hydroxypropyl methylcellulose, 182.5 g of partially saponified polyvinyl alcohol having a degree of saponification of 80.5% by mole and an average degree of polymerization of 2,500, and 73 g of partially saponified polyvinyl alcohol having a degree of saponification of 48% by mole and an average degree of polymerization of 230 were charged. The inside of the polymerization reactor was degassed to an inner pressure of 8 kPa (absolute pressure) and thereafter 730 kg of the vinyl chloride monomer was charged. With stirring, the aqueous liquid including the microcapsule obtained in (1) encapsulating the polymerization initiator was charged in a weight of 400 g in terms of the pure organic peroxide and the temperature rising was simultaneously started by flowing warm water through the jacket. At the stage where the temperature in the polymerization reactor reached 57.0° C., this temperature was retained and the polymerization was continued.

At the time when a polymerization conversion ratio reached 88%, 186 g of 35% by mass aqueous dispersion liquid of triethylene glycol-bis[3-(3-t-butyl-5-methyl-4-hydroxyphenyl)propionate] was added into the polymerization reactor and subsequently the unreacted monomer was recovered. The polymer slurry was dehydrated and dried to give a vinyl chloride polymer.

The apparent specific gravity, the average particle diameter, the plasticizer absorption amount, and the number of fish eyes of the obtained polymer were measured in accordance with the following methods. The results are listed in Table 1.

—Apparent Density—

The apparent density of the sample polymer was measured in accordance with JIS K 7365.

—Average Particle Diameter—

Sieves having a nominal dimension of 300 μm, 250 μm, 180 μm, 150 μm, 106 μm, and 75 μm in the testing sieves prescribed in JIS Z 8801 were attached to a low-tap type sieve shaker. Onto the top sieve, 100 g of the sample polymer was gently poured. After 10-minute shake, the mass of the sample polymer remaining on each of the sieves was measured and percentages (A to F) to the total mass (100 g) were determined.

A: Remaining ratio (%) on the sieve having a nominal dimension of 250 μm
B: Remaining ratio (%) on the sieve having a nominal dimension of 180 μm
C: Remaining ratio (%) on the sieve having a nominal dimension of 150 μm
D: Remaining ratio (%) on the sieve having a nominal dimension of 106 μm
E: Remaining ratio (%) on the sieve having a nominal dimension of 75 μm
F: Passing ratio (%) through the sieve having a nominal dimension of 75 μm The average particle diameter was determined by substituting the determined remaining ratios and the passing ratio of each of the sieves for the following formula.

Average particle diameter (μm)={($A$×300)+($B$×215)+($C$×165)+($D$×128)+($E$×90)+($F$×60)}×(1/100)

—Plasticizer Absorption Amount—

The plasticizer absorption amount of the sample polymer was measured in accordance with JIS K 7386.

—Number of Fish Eyes—

One hundred parts by mass of the sample polymer, 50 parts by mass of bis(2-ethylhexyl)phthalate (DOP), 2.0 parts by mass of Ba/Zn stabilizer, 5.0 parts by mass of epoxidized soybean oil, 0.1 part by mass of carbon black, and 0.5 part by mass of titanium dioxide were mixed to give a compound. With a roll mill, 50 g of this compound was kneaded at 145° C. for 5 minutes to be partially taken as a sheet having a thickness of 0.3 mm. The number of fish eyes was determined by counting the number of clear particles in 100 cm$^2$ of this sheet.

Example 2

The same procedure as the procedure in Example 1 was carried out except that the partially saponified polyvinyl alcohol used in the production of the aqueous liquid including the microcapsule was replaced with partially saponified polyvinyl alcohol having a degree of saponification of 88% by mole and an average degree of polymerization of 3,300. The results are listed in Table 1.

Example 3

The same procedure as the procedure in Example 1 was carried out except that the partially saponified polyvinyl alcohol used in the production of the aqueous liquid including the microcapsule was replaced with partially saponified polyvinyl alcohol having a degree of saponification of 82% by mole and an average degree of polymerization of 2,400. The results are listed in Table 1.

Example 4

The same procedure as the procedure in Example 1 was carried out except that the partially saponified polyvinyl alcohol used in the production of the aqueous liquid including the microcapsule was replaced with partially saponified polyvinyl alcohol having a degree of saponification of 98% by mole and an average degree of polymerization of 1,700. The results are listed in Table 1.

Example 5

The same procedure as the procedure in Example 1 was carried out except that in the production of the microcapsule composition liquid, the materials were replaced with 40 parts by mass of water, 5 parts by mass of an aqueous solution (concentration 10% by mass) of the partially saponified polyvinyl alcohol, and 35 parts by mass of di-(2-ethylhexyl)peroxydicarbonate. The results are listed in Table 1.

Example 6

The same procedure as the procedure in Example 1 was carried out except that the partially saponified polyvinyl alcohol used in the production of the aqueous liquid including the microcapsule was replaced with gelatin. The results are listed in Table 1.

Example 7

The same procedure as the procedure in Example 1 was carried out except that the organic peroxide used in the production of the aqueous liquid including the microcapsule was replaced with t-butyl peroxyneodecanoate. The results are listed in Table 1.

Comparative Example 1

The same procedure as the procedure in Example 1 was carried out except that an isoparaffin solution of di-(2-ethylhexyl)peroxydicarbonate having a concentration of 70% was used instead of the microcapsule composition liquid. The results are listed in Table 1. In this case, the fish eyes of the obtained vinyl chloride polymer increased and thus the quality of the formed product of the vinyl chloride polymer deteriorated.

Comparative Example 2

The same procedure as the procedure in Example 1 was carried out except that the partially saponified polyvinyl alcohol was not used in the production of the microcapsule composition liquid. The results are listed in Table 1. In this case, the microcapsule was not formed but an agglomerate having a median diameter of 200 μm was formed.

In addition, it has been found that the polymerization stability and the basic properties of the vinyl polymer can be retained.

According to the present embodiment, a microcapsule that can reduce fish eyes in the produced vinyl polymer can be provided.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A microcapsule comprising:
a core/shell structure, wherein
the shell includes a water-soluble polymer and the core includes an organic peroxide, and
the water-soluble polymer is at least one water-soluble polymer selected from the group consisting of polyvinyl alcohol, poly(meth)acrylic acid derivatives, polyvinyl pyrrolidone, and polyethylene oxide,
and the organic peroxide has a 10-hour half-life temperature in benzene at a concentration of 0.1 mol/L of 70° C. or less.

2. The microcapsule according to claim 1, wherein the polyvinyl alcohol is partially saponified polyvinyl alcohol having a degree of saponification of 80% by mole or more and 99.5% by mole or less and an average degree of polymerization of 1,500 or more and 3,500 or less.

TABLE 1

| | | | | Example 1 | Example 2 | Example 3 | Example 4 | Example 5 |
|---|---|---|---|---|---|---|---|---|
| Aqueous liquid including microcapsule | Partially saponified polyvinyl alcohol | Degree of saponification | % by mole | 88 | 88 | 82 | 98 | 88 |
| | | Average degree of polymerization | | 1,800 | 3,300 | 2,400 | 1,700 | 1,800 |
| | Organic peroxide *1 | | | A | A | A | A | A |
| | Median diameter | | μm | 4 | 6 | 2 | 8 | 3 |
| Solubility to EDC | | | — | ○ | ○ | ○ | ○ | ○ |
| Vinyl chloride polymer | Apparent specific gravity | | g/ml | 0.570 | 0.572 | 0.568 | 0.577 | 0.574 |
| | Average particle diameter | | μm | 143 | 138 | 156 | 148 | 141 |
| | Plasticizer absorption amount | | % | 22.6 | 22.3 | 22.7 | 22.1 | 22.0 |
| | Number of fish eyes | | Counts | 1 | 3 | 0 | 3 | 5 |

| | | | | Example 6 | Example 7 | Comparative Example 1 | Comparative Example 2 |
|---|---|---|---|---|---|---|---|
| Aqueous liquid including microcapsule | Partially saponified polyvinyl alcohol | Degree of saponification | % by mole | Gelatin | 88 | — | — |
| | | Average degree of polymerization | | | 1,800 | — | — |
| | Organic peroxide *1 | | | A | B | A | A |
| | Median diameter | | μm | 12 | 3 | — | >200 |
| Solubility to EDC | | | — | ○ | ○ | X | X |
| Vinyl chloride polymer | Apparent specific gravity | | g/ml | 0.565 | 0.569 | 0.573 | — |
| | Average particle diameter | | μm | 162 | 147 | 152 | — |
| | Plasticizer absorption amount | | % | 23.0 | 22.8 | 22.5 | — |
| | Number of fish eyes | | Counts | 2 | 0 | 82 | — |

*1 A = di-(2-ethylhexyl)peroxydicarbonate, B = t-butyl peroxyneodecanoate

From the results listed in Table 1, it has been found that, according to the microcapsule of the embodiment, the vinyl polymer having the extremely small number of fish eyes can be obtained in the production of the polymer particularly using the vinyl chloride monomer or the vinyl chloride monomer and the monomer that can be copolymerized with the vinyl chloride monomer among the production of the vinyl polymers to which improved productivity is required.

3. The microcapsule according to claim 1, wherein the microcapsule has a median diameter (D50) of 15 μm or less.

4. A method for producing a microcapsule comprising:
a mixing step of mixing a water-soluble polymer and an organic peroxide to give a microcapsule,
wherein the microcapsule has a core/shell structure, and the shell includes the water-soluble polymer and the core includes the organic peroxide, the water-soluble polymer is at least one water-soluble polymer selected from the group consisting of polyvinyl alcohol, poly(meth)acrylic acid derivatives, polyvinyl pyrrolidone, and polyethylene oxide, and the organic peroxide has a 10-hour half-life temperature in benzene at a concentration of 0.1 mol/L of 70° C. or less.

5. The method for producing a microcapsule according to claim 4, wherein in the mixing step, an aqueous medium is further mixed with the water-soluble polymer and the organic peroxide to give the microcapsule.

6. The method for producing a microcapsule according to claim 5, wherein in the mixing step, the aqueous medium is used in an amount of 30 parts by mass or more and 150 parts by mass or less relative to the 100 parts by mass of the organic peroxide.

7. The method for producing a microcapsule according to claim 4, wherein in the mixing step, the water-soluble polymer is used in an amount of 0.01 parts by mass or more and 25 parts by mass or less relative to the 100 parts by mass of the organic peroxide.

\* \* \* \* \*